United States Patent [19]

Drent

[11] Patent Number: 4,602,105

[45] Date of Patent: Jul. 22, 1986

[54] PROCESS FOR THE PREPARATION OF ALPHA-HALOALKYL ESTERS

[75] Inventor: Eit Drent, Amsterdam, Netherlands

[73] Assignee: Shell Oil Company, Houston, Tex.

[21] Appl. No.: 593,062

[22] Filed: Mar. 26, 1984

[30] Foreign Application Priority Data

May 20, 1983 [GB] United Kingdom ............... 8314001

[51] Int. Cl.$^4$ ..................... C07C 67/14; C07C 67/36; C07C 69/003; C07C 69/007
[52] U.S. Cl. ................................... 560/266; 260/408; 560/1; 560/8; 560/51; 560/55; 560/61; 560/73; 560/100; 560/105; 560/106; 560/121; 560/122; 560/125; 560/126; 560/174; 560/186; 560/187; 560/227; 560/229; 560/263; 568/490
[58] Field of Search ............... 560/8, 51, 55, 61, 266, 560/1, 106, 105, 227, 187, 122, 229, 100, 73, 174, 125, 121; 260/408, 409

[56] References Cited

U.S. PATENT DOCUMENTS 4,221,918 9/1980 Suzuki ................................. 560/263

Primary Examiner—Vivian Garner
Attorney, Agent, or Firm—Ronald R. Reper

[57] ABSTRACT

A process for the preparation of alpha-haloalkylesters, wherein an acylhalide having the general formula

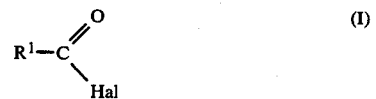

in which $R^1$ represents a substituted or unsubstituted hydrocarbyl group and Hal represents chlorine or bromine is contacted with hydrogen at elevated temperature and pressure in the presence of a catalytic system comprising at least one Group VIII element.

24 Claims, No Drawings

PROCESS FOR THE PREPARATION OF ALPHA-HALOALKYL ESTERS

BACKGROUND OF THE INVENTION

The present invention relates to a process for the preparation of alpha-haloalkyl esters.

Alpha-haloalkyl esters are useful and versatile intermediates having two different reactive groups attached to one carbon atom. They can be used for the preparation of acycloxyalkyl esters by reaction with carboxylic acids or their alkali or silver salts, for example in order to obtain pharmaceuticals (cf. French Demande 2,164,489 or German Offenlegungsschrift 2,706,413). They may also be used for the preparation of alpha-acycloxy nitriles by reaction with alkali cyanides which nitriles can be used as plant protective agents (cf. German Offenlegungsschrift 2,919,974).

Alpha-haloalkyl esters may further be used for the preparation of fulvenes for example by reacting an alpha-haloalkyl ester of acetic acid with sodium cyclopentadienide followed by elimination of acetic acid (cf. Helv. Chim. Acta 54 (1971) pp. 1037–1046). Fulvenes can be applied as anti-knock compounds in fuels for combustion engines (cf. U.S. Pat. No. 2,589,969) or as components of polymer compositions (cf. U.S. Pat. No. 3,390,156).

Alpha-haloalkyl esters have hitherto been prepared by procedures such as chlorination of alkyl esters or addition of a hydrogen halide to alpha-alkenyl esters or by reacting an acyl halide with an aldehyde. The reaction last mentioned appears to be the most useful and widely used method for preparing alpha-haloalkyl esters (cf. Acta. Chem. Scand. 20 (1966) pp. 1273–1280).

It has now been found that alpha-haloalkyl esters can simply be prepared by reacting an acyl halide with hydrogen thereby avoiding the separate preparation of an aldehyde necessary in the known methods mentioned above.

SUMMARY OF THE INVENTION

The present invention therefore provides a process for the preparation of alpha-haloalkyl esters in which an acyl halide having the general formula

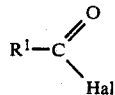

(I)

in which $R^1$ represents a substituted or unsubstituted hydrocarbyl group and Hal represents chlorine or bromine is contacted with hydrogen at elevated temperature and pressure in the presence of a catalytic system comprising at least one Group VIII element.

DESCRIPTION OF PREFERRED EMBODIMENTS

The group $R^1$ containing 1–20 carbon atoms may be an aryl, alkyl, alkaryl or aralkyl group which, optionally, may be substituted with one or more inert substituents such as fluorine or chlorine or alkoxy, phenoxy or alkanoyl groups. Preferably $R^1$ is an alkyl group having 1–20 carbon atoms. Most preferably $R^1$ is an unsubstituted alkyl group having 1–4 carbon atoms. The process of the invention is particularly suitable for the preparation of the alpha-chloroethyl esters of acetic acid from acetyl chloride.

The catalytic system used in the process of the invention comprises preferably palladium, rhodium or ruthenium.

Palladium can be used in a homogeneous catalytic system comprising palladium compounds soluble in the reaction mixture such as palladium chloride dihydrate or organic palladium salts or complexes such as palladium acetate or palladium acetyl-acetonate. Preferably the catalyst system is a heterogeneous catalyst comprising palladium metal on a carrier such as for example carbon.

Rhodium is preferably used in a homogeneous catalytic system comprising a rhodium compound soluble in the reaction mixture. Examples of suitable rhodium compounds are rhodium (III) hydroxide, rhodium (III) chloride, rhodium (III) chloride trihydrate, rhodium (III) bromide, rhodium (III) iodide and the corresponding pyridine and phosphine complexes such as tris(pyridine) rhodium (III) chloride or dichloro bis(triphenylphosphine) rhodium, rhodium (III) formate, rhodium (III) acetate, rhodium (III) butyrate, rhodium (III) naphtenate, dirhodium octacarbonyl, tetrarhodium dodecacarbonyl, hexarhodium hexadecacarbonyl, rhodium dicarbonyl acetylacetonate and other organorhodium complexes. Preference is given to the use of rhodium (III) chloride trihydrate.

Ruthenium is also preferably used in a homogeneous catalytic system comprising a ruthenium compound soluble in the reaction mixture. Examples of suitable ruthenium compounds are ruthenium (III) chloride, ruthenium (III) chloride trihydrate, organic ruthenium salts or complexes such as ruthenium (III) propionate, ruthenium (III) butyrate, ruthenium pentacarbonyl, triruthenium dodecacarbonyl and mixed ruthenium halocarbonyls such as bis-(ruthenium tricarbonyldibromide) and other organoruthenium complexes.

The amount of Group VIII elements to be used in the process of the invention is not critical and any amount which exerts catalytic activity can be used. Amounts as low as 0.001% by wt calculated on the amount of acyl halide

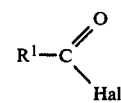

can be used, preference being given to amounts in the range of from 0.005 to 10% by wt, most preferably between 0.01 and 5% by wt on the same basis.

The catalytic system used in the process of the invention may comprise a promoter or combinations of promoters. Suitable promoters are iodide or bromide sources such as for example elemental iodine, elemental bromine, hydrogen iodide, hydrogen bromide and metal iodides or bromides. Examples of metal iodides or bromides comprise iodides or bromides of alkali metals such as lithium iodide or sodium iodide, zinc iodide, zinc bromide, chromium (III) iodide, cobalt (II) iodide and nickel (II) iodide. Other iodide sources which can be used conveniently comprise organic iodine compounds such as alkyl, aryl, aralkyl or acyl iodides having up to 12 carbon atoms. Preference is given to the use of methyl iodide. The quantity of the iodide or bromide source added to the reaction mixture is not crucial.

Suitably the amount of iodide and/or bromide source is in the range of from 0.1 to 1000, preferably from 1 to 500 and especially from 10 to 300 gram atoms I or Br per gram atom Group VIII element.

The process according to the invention may also be carried out in the presence of a catalytic system comprising one or more Group Va compounds as promoters. Suitable Group Va compounds consist of compounds represented by the general formula

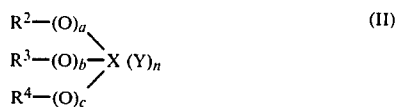
(II)

in which X is a Group Va element having a valency of 3 or higher, selected from N, P, As or Sb; Y is a Group VIa element selected from O, S or Se; n is 0 or 1; either a, b and c are 0 or 1 and $R^2$, $R^3$ and $R^4$ are similar or dissimilar optionally substituted hydrocarbyl groups, or a and b are 0 and c is 0 or 1 and $R^2$ and $R^3$ form together with X a heterocyclic group; or a, b and c are 0 and $R^2$, $R^3$ and $R^4$ form together with X a heterocyclic aromatic ring system. Preference is given to compounds represented by the general formula II in which X is N or P and Y is O and a, b an c are 0. In these compounds the group $R^2$, $R^3$ and $R^4$ are preferably similar or dissimilar alkyl groups containing 1-12 carbon atoms or cycloalkyl, aryl or alkaryl groups containing 5-12 carbon atoms optionally substituted with groups which are substantially inert in the reaction medium such as chlorine, alkoxy groups, carboxylic (ester) groups, oxo groups or sulphone or sulphoxide groups. When X is N, preferably the nitrogen atom and $R^2$, $R^3$ and $R^4$ form together a heterocyclic aromatic ring system.

Very suitable promoters are tertiary amines and the oxides thereof such as triethylamine, tri-n-butylamine, triethylamine oxide, N,N-dimethyl phenylamine, N-methyl piperidine oxide, dimethyl octylamine oxide; amides such as N,N-dimethyl acetamide or N-methyl pyrrolidone (N-methylbutyrolactam); tertiary phosphines and the oxides thereof such as tri-n-butylphosphine, tri-n-butylphosphine oxide, triethylphosphine, triethylphosphine oxide, tricyclohexylphosphine, tricyclohexylphosphine oxide, triphenylphosphine, triphenylphosphine oxide, tri-p-tolylphosphine oxide, tri-p-chloro phenylphosphine; and heterocyclic aromatic nitrogen compounds such as pyridine, pyridine oxide and methyl substituted pyridines and the oxides thereof. Most preferred are triphenylphosphine, triphenylphosphine oxide, pyridine and pyridine oxide.

The amount of Group Va compound represented by the general formula II to be used in the process of the invention is not critical and may be in the range of from 0.01 to 200 moles Group Va compound per gram atom Group VIII element. As stated hereinbefore the catalytic system used in the process of the invention may comprise combinations or promoters. Preference is given to combinations of two or more of the compounds methyl iodide triphenylphosphine and triphenylphosphine oxide.

It will be appreciated that in the reaction mixture salts or complexes may be formed by the reaction of the oxide, sulfide or selenide of the tertiary N, P, As or Sb compounds with the iodine or bromine compound present. Examples of such salts and complexes are alkoxy pyridinium salts for example methoxy pyridinium iodide formed from pyridine oxide and methyl oxide and the complexes $[(C_6H_5)_3PO-H-OP(C_6H_5)_3]^+I_3^-$ or $[(C_2H_5)_3AsO-H-OAs(C_2H_5)_3]^+I^-$. Consequently the use of such salts or complexes when prepared separately is within the scope of the present invention. Furthermore it will be appreciated that the oxides of the phosphines having the formula II can be formed in situ from the corresponding phosphines by carrying out the reaction in the presence of molecular oxygen or hydrogen peroxide.

The process according to the present invention can be carried out using a temperature in the range from about 50° C. to about 250° C. Preference is given to a temperature in the range of 100° C. to 200° C. and particularly in the range of 130° C. to 170° C. The contacting of the staring material with hydrogen according to the invention can be carried out at pressures as low as 5 bar. Pressures in the range of 20 to 100 bar are preferred. Higher pressures, for example pressures as high as 1000 bar, can be applied, but they are generally not economical because of the investments and energy costs involved.

The hydrogen used in the process of the invention may contain inert gases such as for example nitrogen, noble gases, carbon dioxide or methane. In the case that a homogeneous catalyst is used the hydrogen may contain carbon monoxide. The use of mixtures of hydrogen and carbon monoxide, i.e., synthesis gas, has the advantage that such mixtures are easily available. Moreover, when carbon monoxide is present in the reaction mixture, the starting acyl halides may be formed in situ from a halide $R^1Hal$ and carbon monoxide is desired. The amount of carbon monoxide present in the hydrogen is not critical. The molar ratio of carbon monoxide to hydrogen may be in the range of 0 to 10, preferably in the range of 0 to b 2.

The preparation of alpha-haloalkyl esters according to the process of the invention by converting an acyl halide with hydrogen can be expressed by the following chemical equation:

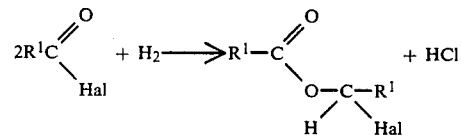

If desired when a homogeneous catalyst is used the formation of HCl can be suppressed by carrying out the reaction in the presence of an ester, preferably having the formula

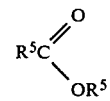

in which $R^5$ is identical to the group $R^1$ in the starting acyl halide

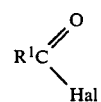

and carbon monoxide. When for example the conversion of acetyl chloride is carried out in the presence of methyl acetate and carbon monoxide the following reaction take place:

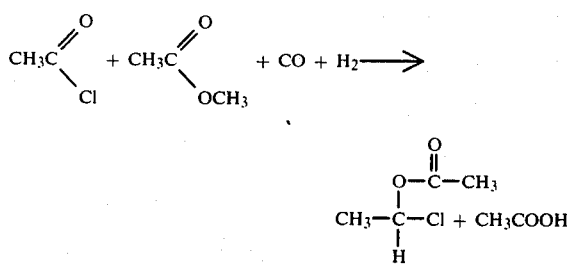

By carrying out the reaction in this way all the chlorine present in the starting acetyl chloride turns up in the product obtained.

The process of the invention may be carried out in the gaseous or liquid phase. Preference is given to the liquid phase. If desired the reaction mixture may contain a solvent. Suitable solvents include carboxylic acids such as acetic acid and propanoic acid, carboxylic acid esters such as methyl acetate and cyclic esters such as butyrolactone. Ethers can also be used as solvent, for example dimethyl ether, diethyl ether, methyl-t-butyl ether, diglyme and tetraglyme, and cyclic ethers such as tetrahydrofuran, 1,4-dioxane, 1,3-dioxane and the dioxalanes. Other compounds which can be used as solvent include sulphones and sulphoxides. Examples of such compounds are dimethyl sulphone, diethyl sulphone, methyl ethyl sulphone, methyl butyl sulphone, sulpholane, 2-methylsulpholane, 3-methyl-sulpholane, 2-methyl-4-butyl sulpholane, dimethyl sulphoxide and diethyl sulphoxide. The reaction time is not critical and will depend on the temperature and the pressure applied. Reaction times of from 0.25 to 30 hours are sufficient, preference being given to reaction times in the range of from 1 to 20 hours. The process according to the invention can be carried out batch wise, semi-continuously or continuously. The reaction section may comprise one or more autoclaves or one or more reactor tubes the walls of which are made of or coated with inert materials. The reaction products may be isolated by techniques known in the art.

The following examples illustrate the invention.

EXAMPLE I

The experiments 1–6 in this example were carried out using the same technique. The conditions and results of these experiments are given in Table A. A Hastelloy C (Trade Mark) 300 ml magnet driven autoclave was charged with acetyl chloride, $RhCl_3.3H_2O$, optionally with triphenylphosphine oxide, a mixture of triphenylphosphine oxide and triphenylphosphine or a mixture of triphenylphosphine oxide and methyl iodide. The vessel was flushed with carbon monoxide and then pressurized with hydrogen and carbon monoxide each having a partial pressure of 20 bar at room temperature. The autoclave was then heated to a fixed temperature and kept at this temperature during a reaction time indicated in Table A. The pressure was maintained during this reaction by feeding in hydrogen.

After the reaction the reaction mixture was analyzed by gas-liquid chromatography; the alpha-chloroethyl ester of acetic acid was produced at a conversion and selectivity as indicated in Table A. The main by-product appeared to be ethylidene diacetate and/or acetaldehyde.

TABLE A

| Exp. | Catalytic system | | | Acetyl chloride ml. | $H_2$ partial pressure bar | CO partial pressure bar | temperature °C. | reaction time hrs. | conversion[1] % | selectivity[2] % |
|---|---|---|---|---|---|---|---|---|---|---|
| | Group VIII metal compound m.mol. | Promotor m.mol. | | | | | | | | |
| 1 | $RhCl_3.3H_2O$ 0.5 | | | 50 | 20 | 20 | 160 | 15 | 10 | 85 |
| 2 | $RhCl_3.3H_2O$ 0.5 | $Ph_3P=O$ | 3 | 50 | 20 | 20 | 160 | 15 | 30 | 90 |
| 3 | $RhCl_3.3H_2O$ 0.5 | $Ph_3P$ $Ph_3P=O$ | 3 0.25 | 50 | 20 | 20 | 160 | 15 | 25 | 90 |
| 4 | $RhCl_3.3H_2O$ 0.5 | $Ph_3P$ $Ph_3P=O$ | 3 0.25 | 50 | 20 | 20 | 150 | 15 | 15 | 90 |
| 5 | $RhCl_3.3H_2O$ 0.5 | $CH_3I$ $Ph_3P$ | 10 1.5 | 50 | 20 | 20 | 135 | 15 | 20 | 90 |
| 6 | $RhCl_3.3H_2O$ 0.5 | | | 25* | 30 | 30 | 150 | 15 | 40 | 60 |

[1]The conversion is calculated as $\frac{\text{moles acetyl chloride reacted}}{\text{moles acetyl chloride initially present}}$

[2]The selectivity is calculated as $\frac{2 \times \text{moles alpha-chloroethyl ester of acetic acid}}{\text{moles acetyl chloride reacted}}$

*acetic acid 25 ml present

EXAMPLE II

A Hastelloy C (Trade Mark) magnet driven autoclave was charged with 25 ml acetyl chloride, 28 ml methyl acetate, 1 mmol $RhCl_3.3H_2O$ and 3 mmol triphenyl phosphine. The vessel was then flushed with carbon monoxide. After pressurizing with hydrogen and carbon monoxide having partial pressures of 20 bar the autoclave was heated to 160° C. and kept at this temperature during 15 hours. The pressure was maintained constant during this time by feeding in hydrogen and carbon monoxide at a ratio of 1:1 corresponding with the partial pressures. After the reaction mixture was analyzed by gas-liquid chromatography the alpha-chloroethyl ester of acetic acid was formed at a conversion of 20% and a selectivity of 85%. The above experiment was repeated except that an amount of 0.25 mmol triphenylphosphine oxide was added as an additional promoter. Conversion and selectivity were 15% and 90% respectively.

The last experiment was repeated except that after flushing an amount of 11.5 g methylchloride was added. The alpha-chloroethyl ester of acetic acid was formed at a conversion of 26% and a selectivity of 92%.

EXAMPLE III

A Hastelloy C (Trade Mark) 300 ml magnet driven autoclave was charged with 50 ml acetyl chloride and 0.5 g of a catalyst consisting of 3% by weight of palladium on carbon. After flushing with carbon monoxide and pressurizing to 50 bar with hydrogen the vessel was heated to 150° C. The vessel was kept at this temperature during 2.5 hours maintaining the pressure at 50 bar by feeding in hydrogen. Gas-liquid chromatography analysis of the reaction mixture showed that the alpha-chloroethyl ester was produced at a conversion of 100% and a selectivity of 60%. The above experiment was repeated except that the temperature of the vessel was kept at 90° C. during 15 hours. The alpha-chloroethyl ester of acetic acid was produced at a conversion of 80% and a selectivity of 85%.

I claim:

1. A process for the preparation of alpha-haloalkyl esters, characterized in that an acylhalide having the general formula

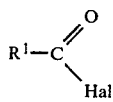

(I)

in which R$^1$ represents a hydrocarbyl group containing 1–20 carbon atoms and Hal represents chlorine or bromine is contacted with hydrogen at a temperature from about 50° to about 250° C. and pressure from about 5 to about 1000 bar in the presence of a Group VIII element catalyst comprising a homogeneous palladium catalyst, a heterogeneous palladium catalyst, a homogeneous rhodium catalyst or a homogeneous ruthenium catalyst.

2. A process according to claim 1, wherein R$^1$ is an alkyl group having 1–20 carbon atoms.

3. A process according to claim 1, wherein R$^1$ is an alkyl group having 1–4 carbon atoms.

4. A process according to claim 1, wherein the acylhalide

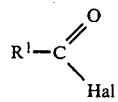

is acetyl chloride.

5. A process according to claim 1, wherein the catalyst is a heterogeneous catalyst comprising palladium metal on a carbon carrier.

6. A process according to claim 1, wherein the catalyst is a homogeneous catalyst comprising a rhodium compound soluble in the reaction mixture.

7. A process according to claim 6, wherein the catalyst comprises rhodium III chloride trihydrate.

8. A process according to claim 1, wherein the amount of Group VIII element is in the range of from 0.005 to 10% by wt calculated on the amount of acyl halide

9. A process according to claim 1, wherein the temperature is in the range of 100° C. to 200° C.

10. A process according to claim 1, wherein the pressure is in the range of 20 to 100 bar.

11. A process for the preparation of alpha-haloalkyl esters, characterized in that an acylhalide having the general formula

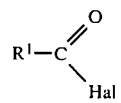

(I)

in which R$^1$ represents a hydrocarbyl group containing 1–20 carbon atoms and Hal represents chlorine or bromine is contacted with hydrogen at a temperature from about 50° to about 250° C. and pressure from about 5 To about 1000 bar in the presence of a Group VIII element catalyst comprising a homogeneous palladium catalyst, a heterogeneous palladium catalyst, a homogeneous rhodium catalyst or a homogeneous ruthenium catalyst and a promoter selected from an iodide or bromide source.

12. A process according to claim 11, wherein the promoter is methyl iodide.

13. A process according to claim 11, wherein the amount of iodide or bromide source is in the range of from 1 to 500 gram atoms I or Br per gram atom Group VIII element.

14. A process for the preparation of alpha-haloalkyl esters, characterized in that an acyl halide having the general formula

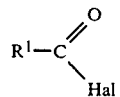

in which R$^1$ represents a hydrocarbyl group containing 1–20 carbon atoms and Hal represents chlorine or bromine is contacted with hydrogen at a temperature from about 50° to about 250° C. and pressure from about 5 to about 1000 bar in the presence of a homogeneous catalyst selected from the group consisting of a homogeneous palladium catalyst, a homogeneous rhodium catalyst and a homogeneous ruthenium catalyst and carbon monoxide.

15. A process according to claim 14, wherein the molar ratio of carbon monoxide to hydrogen is a positive number in the range of 0 to 10.

16. A process for the preparation of alpha-haloalkyl esters, characterized in that an acyl halide having the general formula

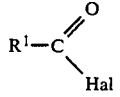

in which R$^1$ represents a hydrocarbyl group containing 1–20 carbon atoms and Hal represents chlorine or bromine is contacted with hydrogen at a temperature from about 50° to about 250° C. and pressure from about 5 to about 1000 bar in the presence of a homogeneous catalyst selected from the group consisting of a homogeneous palladium catalyst, a homogeneous rhodium catalyst and a homogeneous ruthenium catalyst and both an ester having the general formula

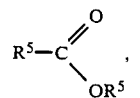

(III)

in which $R^5$ is identical to the group $R^1$ in the starting acyl halide,

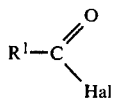

and carbon monoxide are present in the reaction mixture.

17. A process according to claim 16, wherein the acyl halide

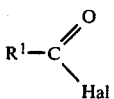

is formed in situ from the halide $R^1Hal$.

18. A process according to claim 16, wherein each of $R^1$ and $R^5$ is a methyl group.

19. A process for the preparation of alpha-haloalkyl esters, characterized in that an acyl halide having the general formula

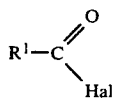 (I)

in which $R^1$ represents a hydrocarbyl group containing 1-20 carbon atoms and Hal represents chlorine or bromine is contacted with hydrogen at a temperature from about 50° to 250° C. and a pressure from about 5 to 1000 bar in the presence of a Group VIII element catalyst comprising a homogeneous palladium catalyst, a heterogeneous palladium catalyst, a homogeneous rhodium catalyst or a homogeneous ruthenium catalyst and a promoter selected from the group consisting of Group Va compounds represented by the general formula:

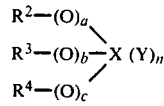 (II)

in which X is a Group Va element having a valency of 3 or higher selected from N and P, Y is the Group VIa element O, a, b and c are O, n is 0 or 1 and $R^2$, $R^3$ and $R^4$ are similar or dissimilar alkyl groups containing 1-12 carbon atoms or cycloalkyl containing 5-12 carbon atoms or aryl groups containing 6-12 carbon atoms.

20. A process according to claim 19, wherein the promoter is a tertiary phosphine or an oxide thereof.

21. A process according to claim 20, wherein the promoter is a triarylphosphine or the oxide thereof.

22. A process according to claim 21, wherein the promoter is triphenylphosphine or triphenyl phosphine oxide.

23. A process according to claim 19, wherein the amount of Group Va compound having the general formula II is in the range of from 0.01 to 200 moles Group Va compound per gram atom Group VIII element.

24. A process for the preparation of alpha-haloalkyl esters characterized in that an acyl halide having the general formula

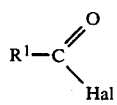 (I)

in which $R^1$ represents a hydrocarbyl group containing 1-20 carbon atoms and Hal represents chlorine or bromine is contacted with hydrogen at a temperature from about 50° to about 250° C. and a pressure from about 5 to about 1000 bar in the presence of a Group VIII element catalyst comprising a homogeneous palladium catalyst, a heterogeneous palladium catalyst, a homogeneous rhodium catalyst or a homogenous ruthenium catalyst and a promoter selected from: pyridine, pyridine oxide, n-methylpiperidine oxide and methyl substituted pyridines and the oxides thereof.

* * * * *